US008151575B2

(12) United States Patent
Wu et al.

(10) Patent No.: US 8,151,575 B2
(45) Date of Patent: Apr. 10, 2012

(54) TEMPERATURE VARIATION APPARATUS

(75) Inventors: Yu-Min Wu, Taipei County (TW); Yi-Chin Tsai, Banciao (TW); Kwan-Chiao Liao, Banqiao (TW)

(73) Assignee: Quanta Computer Inc., Tao Yuan Shien (TW)

( * ) Notice: Subject to any disclaimer, the term of this patent is extended or adjusted under 35 U.S.C. 154(b) by 563 days.

(21) Appl. No.: 12/453,306

(22) Filed: May 6, 2009

(65) Prior Publication Data

US 2010/0101237 A1 Apr. 29, 2010

(30) Foreign Application Priority Data

Oct. 24, 2008 (TW) .............................. 97141016 A

(51) Int. Cl.
*F25B 21/02* (2006.01)
*F28F 1/20* (2006.01)
*C12M 3/00* (2006.01)
*B01L 3/00* (2006.01)

(52) U.S. Cl. ......... 62/3.2; 165/181; 435/287.2; 422/552

(58) Field of Classification Search ..................... 62/3.2; 165/181; 435/287.1, 287.2; 422/552; 219/201
See application file for complete search history.

(56) References Cited

U.S. PATENT DOCUMENTS

| | | | | |
|---|---|---|---|---|
| 6,337,435 | B1 * | 1/2002 | Chu et al. | 136/242 |
| 7,771,933 | B2 * | 8/2010 | Arciniegas et al. | 435/6.11 |
| 2004/0043479 | A1 | 3/2004 | Briscoe et al. | |

FOREIGN PATENT DOCUMENTS

TW 200624562 7/2006

OTHER PUBLICATIONS

English language translation of abstract of TW 200624562.

* cited by examiner

*Primary Examiner* — Chen Wen Jiang

(74) *Attorney, Agent, or Firm* — Thomas, Kayden, Horstemeyer & Risley, LLP

(57) ABSTRACT

The invention discloses a temperature variation apparatus for varying the temperature of a liquid. The temperature variation apparatus includes a metal tube, a power supply, a heat conductor, and a thermo-electric cooler (TEC). The liquid is poured into the metal tube. The power supply has an anode and a cathode respectively connected to two ends of the metal tube, so that the metal tube can be electrified to generate heat. The heat conductor encircles and contacts with the metal tube, and the thermo-electric cooler contacts with the heat conductor.

13 Claims, 3 Drawing Sheets

TEMPERATURE VARIATION APPARATUS

BACKGROUND OF THE INVENTION

1. Field of the Invention

The present invention relates generally to a temperature variation apparatus, and more particularly, relates to a temperature variation apparatus for varying and controlling a temperature of a liquid.

2. Description of the Prior Art

Since the number of sequenced genomes is growing and more disease genes are found, molecular biology is a key knowledge in molecular diagnosis technology and medical diagnosis. Since the technique of polymerase chain reaction (PCR) was developed, molecular biology has been playing an important role in molecular medical diagnostics. Recently, the demand in molecular biological diagnosis and medical clinical diagnosis are growing, the precise and fast quantitative analysis technology is one of the key issues. In the scope of molecular medical diagnosis, real-time PCR is a main technology and has advantages of short testing time, high sensitivity, and various clinical specimens.

When the PCR is carried on, a thermo-cycle is repeated (e.g. denaturation, annealing, and extension), so the high sensitivity of the real-time PCR needs a heat conduction device with stable and precise thermal-control. Therefore, a temperature variation apparatus capable of quickly raising/decreasing temperature and precisely controlling temperature is crucial for the real-time PCR.

Traditionally, several plastic tubes filled with liquid are disposed on a heating region of a temperature variation apparatus, and then a heat source heats the heating region to heat the plastic tubes. In other words, the heat source heats the liquid in the plastic tubes through heating the region. Therefore, the actual temperature of the liquid is calculated based on the temperature of the heating region and some empirical calculations (results of experiments). Thus, it is hard to determine the temperature of the liquid precisely. Additionally, the plastic tubes are heated by one single heating region and thus it is difficult to individually control the temperature of each tube. Due to the fact that there is a certain area in the heating region the heat source heats only , the temperatures of different parts of the heating region are not consistent and have a gradient distribution, which results in the difficulty to precisely control the temperature of each tube.

To sum up, a traditional temperature variation apparatus does not satisfy the requirement of precise temperature control for real-time PCR. Thus the present invention provides a temperature variation apparatus capable of precisely varying and controlling temperature to solve the abovementioned problems.

SUMMARY OF THE INVENTION

Accordingly, an aspect of the present invention is to provide a temperature variation apparatus for precisely controlling and varying a temperature of a liquid.

According to an embodiment of the invention, the temperature variation apparatus for varying a temperature of a liquid comprises a metal tube, a power supply, a heat conductor, and a thermo-electric cooler (TEC). The metal tube is used for holding a liquid. The power supply has an anode and a cathode respectively connected to two ends of the metal tube, for heating the metal tube through electricity. The heat conductor encircles and contacts with the metal tube, and the thermo-electric cooler contacts with the heat conductor.

Moreover, the temperature variation apparatus further comprises a non-contact thermometer and a temperature controller. The non-contact thermometer aims at an opening of the metal tube for determining the temperature of the liquid. The temperature controller is electrically connected with the power supply, the thermo-electric cooler, and the non-contact thermometer. Additionally, the temperature controller selectively adjusts the voltage of the power supply and the voltage of the thermo-electric cooler according to the temperature of the liquid and a predetermined temperature.

To sum up, the temperature variation apparatus of the invention can easily vary the temperature of the liquid due to the lower specific heat of the metal tube and the electrifying of the metal tube for directly heating the liquid. Additionally, the present invention adjusts the heating rate of the metal tube by controlling the voltage of the power supply and adjusts the cooling rate of the metal tube by controlling the voltage of the TEC. Therefore, the temperature variation apparatus of the invention can easily control the temperature and the temperature variation of the liquid to satisfy the thermal-control requirement of the real-time PCR.

The objective of the present invention will no doubt become obvious to those of ordinary skill in the art after reading the following detailed description of the preferred embodiment, which is illustrated in the various figures and drawings.

BRIEF DESCRIPTION OF THE APPENDED DRAWINGS

DETAILED DESCRIPTION OF THE INVENTION

In order to help understanding the invention, there are four description blocks as followed, A: temperature variation (heating), B: temperature variation (cooling), C: temperature control, and D: regional temperature control.

A: Temperature Variation (Heating)

Generally, a temperature variation apparatus is used for varying a temperature of a specific object. In the present invention, the specific object is a liquid 4 shown in FIG. 1. Generally, the liquid 4 is not a fixed body, so the temperature variation apparatus includes a component such as the metal tube 30 shown in FIG. 1 to hold the liquid 4. Due to the smaller specific heat of the metal material, it is easy to raise or lower temperature of the metal tube 30. Thus the temperature variation and temperature variation rate are easy to control. Generally, the metal tube 30 holds a little liquid 4 (about 30 μl~50 μl), so the temperature variation of the metal tube 30 is quite equivalent to the temperature variation of the liquid 4.

It should be noticed that if the temperature variation apparatus 3 of the invention is applied to real-time PCR, because the liquid 4 for PCR contains organism (for example, DNA), the material of the metal tube 30 used should not release poisonous substances for organism at high temperature, and the preferred material can be aluminum, copper, or gold. In another embodiment, the inner wall of the metal tube 30 can be coated with a material with stable chemical property, for example, GaN, to isolate poisonous substances released from the metal tube 30 at high temperature. Thus, even if the metal tube releases poisonous substances, the coating can prevent the poison substances from being released to the liquid 4. Therefore, the suitable material and the suitable coating can lower the influence of the container on real-time PCR.

Figure 1:
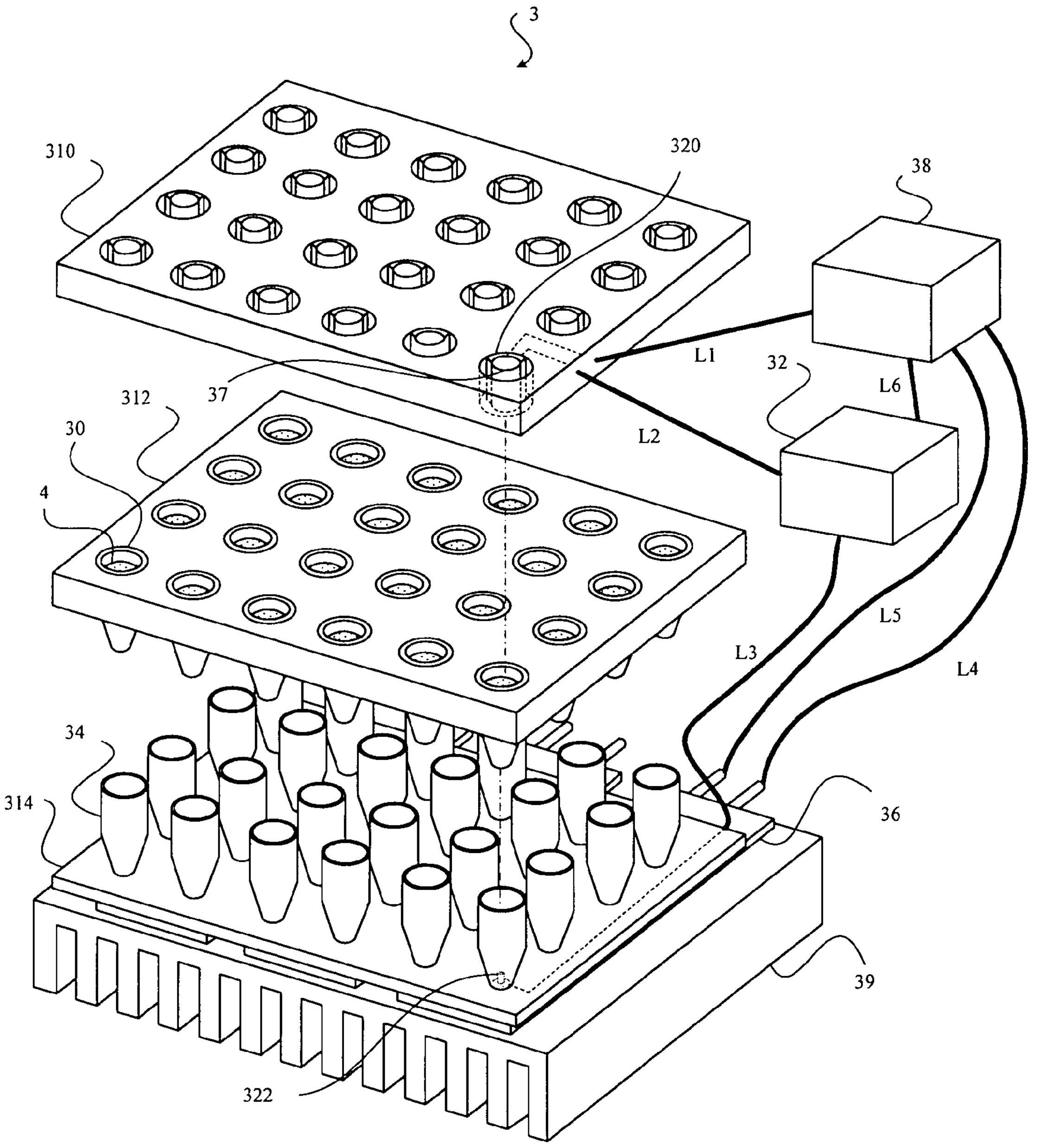
FIG. 1 illustrates a temperature variation apparatus according to one embodiment of the invention.

Additionally, it should be a metal conductive and low in resistance. It is easy to control the amount of heat energy generated by the electrified metal tube 30 to properly heat the held liquid by request. In the invention, the heating component of the temperature variation apparatus 3 is a power supply 32 shown in FIG. 1. Of course, two ends of the metal tube 30 need to be connected with a cathode and an anode, and then the metal tube 30 is electrified to generate heat. In the embodiment, as shown in FIG. 1 and FIG. 2, the anode (not shown in figure) of the power supply 32 is connected with an anode joint 320 via a wire L2; the cathode (not shown in figure) of the power supply 32 is connected with a cathode joint 322 via a wire L3; and voltage is applied across the anode joint 320 and the cathode joint 322 by the power supply 32.

Figure 2:
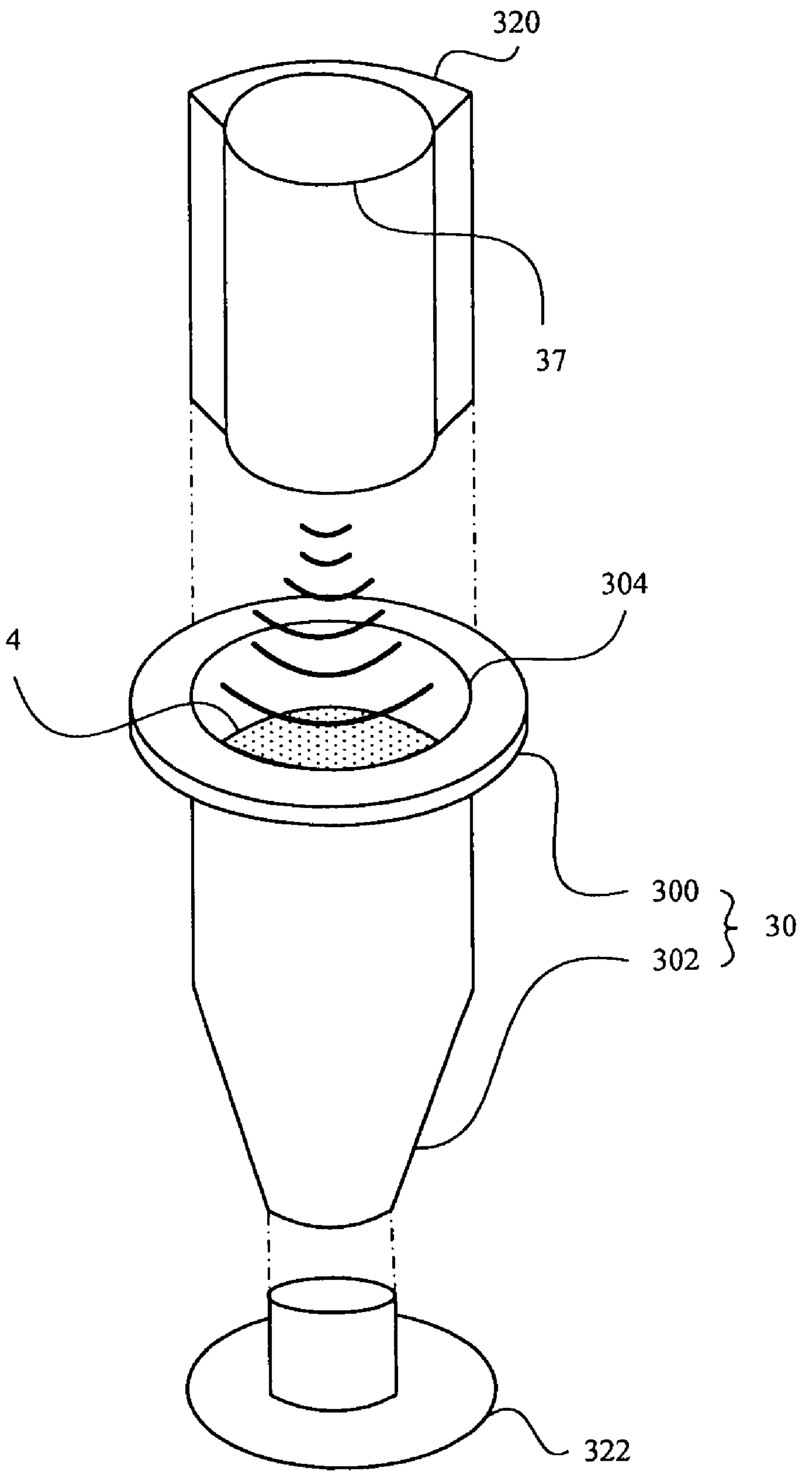
FIG. 2 illustrates the anode joint, the metal tube, and the cathode joint shown in FIG. 1.

The relationship among the anode joint 320, the cathode joint 322, and the metal tube 30 is illustrated in FIG. 2. Meanwhile, please refer to FIG. 1 and FIG. 3. The anode joint 320 is mounted on a first insulation mounting base 310, the metal tube 30 is mounted on a second insulation mounting base 312, and a heat conductor is mounted on a third insulation mounting base. After the first insulation mounting base 310 moves toward and gets close to the second insulation mounting base 312, the anode joint 320 could contact with a metal ring 300 which encircles an opening 304 of the metal tube 30. After the second insulation mounting base 312 moves toward and gets close to the third insulation mounting base 314, the metal tube 30 can be disposed in the heat conductor 34. Thus the cathode joint 322 disposed in the heat-conductor 34 could contact with a cone part 302 of the metal tube 30. Thereby the power supply 32 could be electrically connected with the metal tube 30 via the anode joint 320 and the cathode joint 322, so that current can flow through the metal tube 30 (i.e. a resistance) to generate heat.

B: Temperature Variation (Cooling)

Additionally, the temperature variation apparatus 3 not only heats the liquid 4 but also needs to cool the liquid 4. However, general cooling methods such as passive cooling (e.g. radiator fin), air-cooling (e.g. fan), and water-cooling (e.g. flowing liquid) can not precisely control the temperature drop and the cooling rate. Therefore, the temperature variation apparatus 3 of the invention attains a goal of decreasing temperature precisely via a thermo-electric cooler (TEC) 36. Generally, the thermo-electric cooler 36 consists of a semiconductor. When a voltage is applied across the thermo-electric cooler 36, it results in the temperature of one side of the thermo-electric cooler 36 being higher than the temperature of the other side. Therefore, the metal tube 30 can be put in contact with the cooler side of the thermo-electric cooler 36 to cool itself. Of course, the hotter side of the thermo-electric cooler 36 could be put in contact with a radiator fin 39 as shown in FIG. 1 to avoid overheating.

Figure 3:
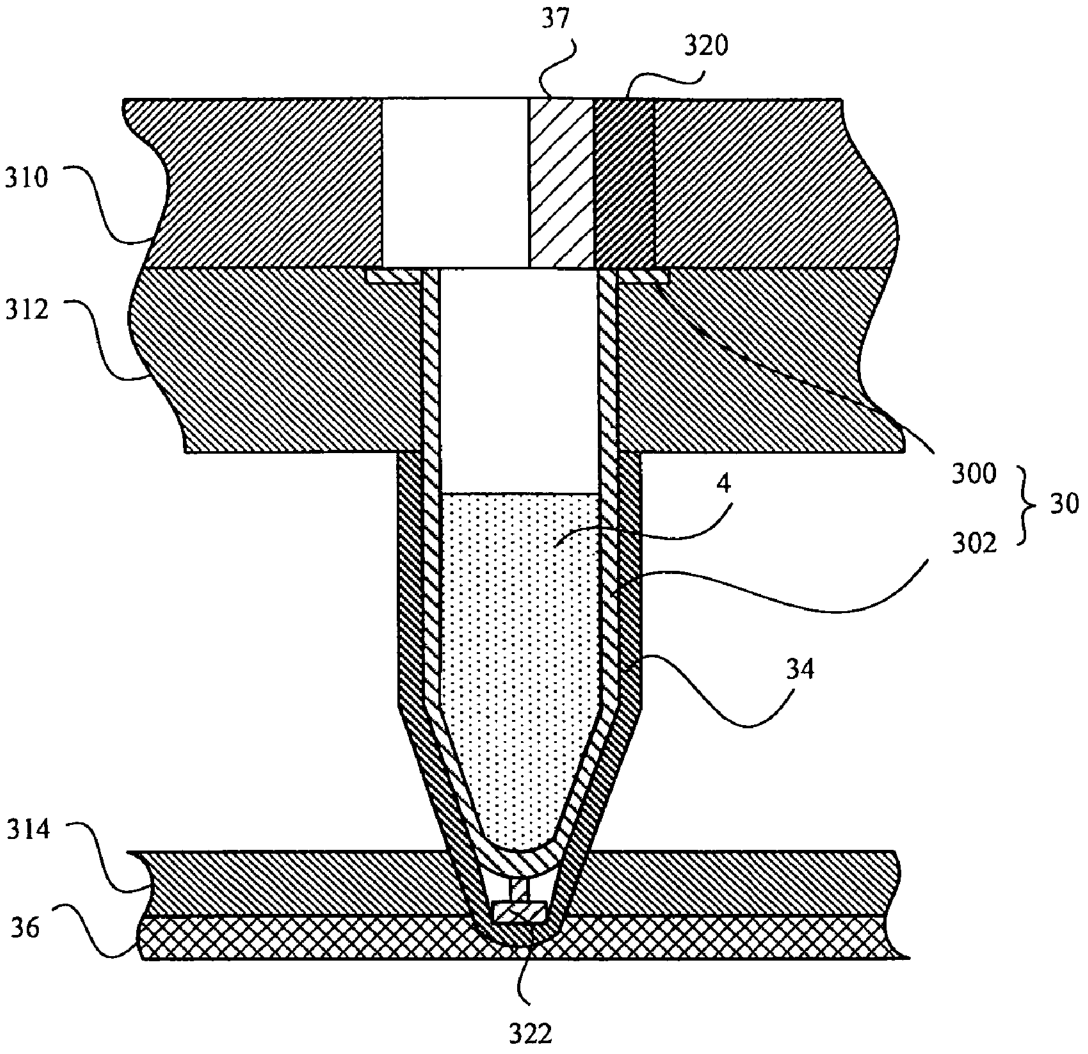
FIG. 3 is a cross-section of the temperature variation apparatus shown in FIG. 1.

It should be noticed that the material of the metal tube 30 is not selected from materials with high conductivity but selected from materials that do not release poisonous substances at high temperature. The thermo-electric cooler 36 does not completely cover the metal tube 30, and the metal tube 30 does not necessarily consist of a material with the highest conductivity. In order to cool the metal tube 30 quickly, the heat conductor 34 encircles and contacts with the metal tube 30, the heat is conducted by the heat conductor 34 from the metal tube 30 to the cooler side of thermo-electric cooler 36 as shown in FIG. 3. In other words, the heat conductor 34 is disposed between the metal tube 30 and the thermo-electric cooler 36 as a heat-transferring medium. By doing so, the heat could be conducted rapidly from the metal tube 30 to the thermo-electric cooler 36.

C: Temperature Control

The aforementioned description discloses the major parts of the temperature variation apparatus 3. However, in order to precisely control the temperature of the liquid 4, the temperature variation apparatus 3 further includes a temperature feedback component and a temperature control component. The temperature feedback component transmits the measurement temperature of the liquid 4 to the temperature control component. Thus, the temperature control component decreases or increases the temperature of the liquid 4 properly according to the measurement temperature and a target temperature.

In the embodiment, the temperature feedback component is a non-contact thermometer 37 such as an infrared thermometer. As shown in FIG. 2 and FIG. 3, the non-contact thermometer 37 aims at an opening 304 of the metal tube 30 and emits a signal (for example, infrared) toward the opening 304, and then determines the temperature of the liquid 4 according to the reflected signal. The non-contact thermometer 37 does not contact with the liquid 4, thus it does not affect the liquid 4 while measuring the temperature of the liquid 4, so as to lower the impact of the temperature measurement on PCR.

Moreover, the temperature control component of the invention is a temperature controller 38. As shown in FIG. 1, the temperature controller 38 is electrically connected to the power supply 32 via a wire L6; connected with the thermo-electric cooler 36 via a wire L4 and a wire L5; and connected with the non-contact thermometer 37 via the wire L1. Several target temperatures and the sequence among these target temperatures are predetermined and stored in the temperature controller 38. The temperature controller 38 adjusts the voltage of the power supply 32 (corresponding to the heating rate) and the voltage thermo-electric cooler 36 (corresponding to the cooling rate) according to the target temperatures and the temperature measured by the non-contact thermometer 37. Therefore, the temperature controller 38 can periodically raise and lower the temperature of the liquid 4 to satisfy the requirement of the real-time PCR. If the temperature (e.g. 30° C.) of the liquid 4 is lower than the target temperature (e.g. 70° C.), the temperature controller 38 can increase the voltage of the power supply 32 and meanwhile decreases the voltage of thermo-electric cooler 36 to raise the temperature of the liquid 4. On the contrary, if the temperature of the liquid 4 is higher than the target temperature, the temperature controller 38 can decrease the voltage of the power supply 32 and meanwhile increases the voltage of thermo-electric cooler 36 to lower the temperature of the liquid 4. Additionally, if the user wants to keep the temperature of the liquid 4 and the temperature is higher than the room temperature, the temperature controller 38 can tune the voltage of the power supply 32 and decreases the voltage of the thermo-electric cooler 36 to tune the heating rate of the metal tube 30 to meet the spontaneous cooling rate.

The temperature is a crucial variable for the real-time PCR, so the precision of the temperature control is relative to the precision of the real-time PCR experiment. Generally, when the temperature is raised or lowered to a target temperature, the actual temperature will oscillate around the target temperature. For example, the target temperature is 40° C., but the actual temperature in sequence may be 41° C., 40.5° C., 39.7° C., and 40.2° C. For the real-time PCR, the oscillation of the temperature affects the experiment a lot. Therefore, the prevent invention utilizes the metal tube, the power supply, and the thermo-electric cooler to avoid the oscillation phenomenon of the temperature for improving the precision of the real-time PCR experiment.

D: Regional Temperature Control

Generally, the real-time PCR might have kinds of controlled variables such as the proportion of different composition in the liquid, the timing of temperature variation, the target temperature, and the temperature variation rate. Because only one controlled variable could be changed in one experiment, it takes a lot of time to repeat experiments with different controlled variables.

The temperature variation apparatus of the invention has several thermo-electric coolers 36, and the power supply 32 has several electrode pairs (not shown). Each electrode pair includes an anode and a cathode corresponding to an anode joint and a cathode joint respectively. Each of the electrode pairs is electrically connected with one of the metal tubes 30. Therefore, the temperature variation apparatus 3 of the invention could respectively control temperature variation rates and temperature variations of the metal tubes 30 at the same time. For example, the liquids 4 held in different metal tubes can be heated to different target temperatures at the same time.

As shown in FIG. 1, three thermo-electric coolers 36 are disposed below the third insulation mounting base 314. Each of the thermo-electric coolers 36 contacts with eight heat conductors 34 to cool the eight metal tubes 34 disposed in the heat conductors 34. Therefore, the temperature variation 3 is divided into three regions for different experiments with different temperature variables such as raising temperature, holding temperature and lowering temperature. Of course, the temperature variation apparatus 3 of the invention not only controls regional temperature but it can also respectively control the temperature of each metal tube 30.

There is an additional remark. The power supply 32 shown in FIG. 1 is connected with single anode joint 320 and single thermo-electric cooler 36; the controller 38 shown in FIG. 1 is electrically connected with single non-contact thermometer 37. In fact, the power supply 32 can be electrically connected with all anode joints 320 and all thermo-electric coolers 36, and the temperature controller 38 could be electrically connected with all non-contact thermometers 37.

Therefore, the temperature variation apparatus 3 of the invention can control the temperature regionally, and different experiments with different controlled variables can be carried out at the same time. Thereby, the temperature variation apparatus 3 of the invention adequately utilizes every temperature variation component and every temperature control component to reduce the whole experiment time.

Compared with the prior art, the temperature variation apparatus of the invention can easily vary the temperature of the liquid due to the lower specific heat of the metal tube and the electrifying of the metal tube for directly heating the liquid. Additionally, the present invention adjusts the heating rate of the metal tube by controlling the voltage of the power supply and adjusts the cooling rate of the metal tube by controlling the voltage of the TEC. Therefore, the temperature variation apparatus of the invention can easily control the temperature and the temperature variation of the liquid to satisfy the thermal-control requirement of the real-time PCR. In addition, the temperature variation apparatus of the invention utilizes several TEC and several electrode pairs to control temperature regionally, and furthermore different experiments with different controlled variables can be carried out at the same time to reduce the whole experiment time.

Although the present invention has been illustrated and described with reference to the preferred embodiment thereof, it should be understood that it is in no way limited to the details of such embodiment but is capable of numerous modifications within the scope of the appended claims.

What is claimed is:

1. A temperature variation apparatus, for varying a temperature of a liquid, comprising:
- a metal tube for holding the liquid;
- a power supply having an anode and a cathode respectively electrically connected to two ends of the metal tube, for heating the metal tube through electricity;
- a heat conductor encircling and contacting with the metal tube; and
- a thermo-electric cooler contacting with the heat conductor.

2. The temperature variation apparatus of claim 1, further comprising a non-contact thermometer aiming at one opening of the metal tube for determining the temperature of the liquid.

3. The temperature variation apparatus of claim 2, further comprising a temperature controller electrically connected with the power supply, the thermo-electric cooler, and the non-contact thermometer, wherein the temperature controller selectively adjusts the voltage of the power supply and the voltage of the thermo-electric cooler according to the temperature of the liquid and a predetermined temperature.

4. The temperature variation apparatus of claim 1, further comprising a radiator fin contacting with the thermo-electric cooler, and the thermo-electric cooler being disposed between the heat conductor and the radiator fin.

5. The temperature variation apparatus of claim 1, wherein two ends of the metal tube comprise a metal ring and a cone part respectively, the metal ring encircles an opening of the metal tube and the power supply electrically connects with the metal ring and the cone part.

6. A temperature variation apparatus, comprising:
- a plurality of metal tubes, one of the metal tubes for holding a liquid of a temperature;
- a power supply with a plurality of electrode pairs, wherein each of the electrode pairs has an anode and a cathode respectively connected to two ends of one of the metal tubes for heating the metal tube by electricity;
- a plurality of heat conductor, each of the heat conductors encircling and contacting with one of the metal tubes; and
- a plurality of thermo-electric coolers, each of the thermo-electric coolers contacting with at least one heat conductor.

7. The temperature variation apparatus of claim 6, further comprising a plurality of non-contact thermometers, each of the non-contact thermometers aiming at one opening of one of the metal tubes for determining the temperature of the liquid.

8. The temperature variation apparatus of claim 7, further comprising a temperature controller electrically connected with the power supply, the thermo-electric coolers, and the non-contact thermometers, wherein the temperature controller selectively adjusts the voltage of the power supply and the voltage of one of the thermo-electric coolers according to the temperature of the liquid and a predetermined temperature.

9. The temperature variation apparatus of claim 7, further comprising a first insulation mounting base, the non-contact thermometers being mounted on the first insulation mounting base.

10. The temperature variation apparatus of claim 6, further comprising a radiator fin contacting with the thermo-electric coolers, and the thermo-electric coolers being disposed between the heat conductor and the radiator fin.

11. The temperature variation apparatus of claim 6, wherein two ends of the metal tube comprises a metal ring and a cone part respectively, the metal ring encircles an opening of the metal tube, and one of the electrode pairs of the power supply electrically connects with the metal ring and the cone part.

12. The temperature variation apparatus of claim 6, further comprising a second insulation mounting base, the metal tubes being mounted on the second insulation mounting base.

13. The temperature variation apparatus of claim 6, further comprising a third insulation mounting base, the heat conductor being mounted on the third insulation mounting base.

* * * * *